(12) United States Patent
Fan et al.

(10) Patent No.: US 11,305,051 B2
(45) Date of Patent: Apr. 19, 2022

(54) FAT CUTTER AND INTEGRATED MACHINE FOR PREPARATION OF IN VITRO FINE-PARTICLE FAT

(71) Applicant: XIANGYA HOSPITAL CENTRAL SOUTH UNIVERSITY, Changsha (CN)

(72) Inventors: Pengju Fan, Changsha (CN); Zhen Li, Changsha (CN); Man Fang, Changsha (CN); Jingjing Li, Changsha (CN)

(73) Assignee: XIANGYA HOSPITAL CENTRAL SOUTH UNIVERSITY, Changsha (CN)

( * ) Notice: Subject to any disclaimer, the term of this patent is extended or adjusted under 35 U.S.C. 154(b) by 0 days.

(21) Appl. No.: 17/415,748

(22) PCT Filed: Jan. 17, 2020

(86) PCT No.: PCT/CN2020/072819
§ 371 (c)(1),
(2) Date: Jun. 18, 2021

(87) PCT Pub. No.: WO2021/062967
PCT Pub. Date: Apr. 8, 2021

(65) Prior Publication Data
US 2022/0040399 A1    Feb. 10, 2022

(30) Foreign Application Priority Data

Sep. 30, 2019   (CN) .......................... 201910942443.5

(51) Int. Cl.
*A61M 1/00*    (2006.01)
*B01D 35/28*   (2006.01)
(Continued)

(52) U.S. Cl.
CPC ............. *A61M 1/892* (2021.05); *B01D 29/76* (2013.01); *B01D 35/28* (2013.01); *B01D 35/30* (2013.01);
(Continued)

(58) Field of Classification Search
CPC ........ A61M 1/89; A61M 1/892; A61M 1/895; A61M 2205/3365; A61M 2205/502;
(Continued)

(56) References Cited

U.S. PATENT DOCUMENTS 5,786,207 A  * 7/1998 Katz ...................... C12M 45/02
                                                              435/267
6,316,247 B1 * 11/2001 Katz ................... A61L 27/3604
                                                              210/446
(Continued)

FOREIGN PATENT DOCUMENTS

CN      106957816 A      7/2017
CN      108014384 A      5/2018
(Continued)

OTHER PUBLICATIONS

Patricia A. Zuk, et al., Multilineage Cells from Human Adipose Tissue: Implications for Cell-Based Therapies, Tissue Engineering, 2001, pp. 211-228, vol. 7 No. 2.

*Primary Examiner* — Benjamin J Klein
(74) *Attorney, Agent, or Firm* — Bayramoglu Law Offices LLC

(57) ABSTRACT

A fat cutter and an integrated machine for preparation of in vitro fine-particle fat are provided. The fat cutter includes a fat inlet channel, a fat outlet channel, at least one set of blades disposed between an outlet of the fat inlet channel and an inlet of the fat outlet channel, and a housing that seals a space in which the outlet of the fat inlet channel, the inlet of the fat outlet channel, and the blades are located. A fat (Continued)

inlet of the fat inlet channel is connected to a large-diameter liposuction tube by a liposuction channel, and a fat outlet of the fat outlet channel is connected to a high-negative pressure device. The outlet of the fat inlet channel and the inlet of the fat outlet channel are oppositely provided, and a gap therebetween matches the thickness of the blades.

20 Claims, 7 Drawing Sheets

(51) Int. Cl.
  *B01D 35/30* (2006.01)
  *B01D 29/76* (2006.01)
  *B02C 18/18* (2006.01)
  *B02C 18/12* (2006.01)

(52) U.S. Cl.
  CPC .............. *B02C 18/12* (2013.01); *B02C 18/18* (2013.01); *A61M 2205/3365* (2013.01); *A61M 2205/502* (2013.01); *B01D 2201/29* (2013.01)

(58) Field of Classification Search
  CPC ........ B01D 29/76; B01D 35/28; B01D 35/30; B01D 2201/29; B02C 18/12; B02C 18/18
  See application file for complete search history.

(56) References Cited

U.S. PATENT DOCUMENTS

| | | | |
|---|---|---|---|
| 7,749,741 B2* | 7/2010 | Bullen | C12M 45/02 |
| | | | 435/183 |
| 10,336,980 B2* | 7/2019 | Cimino | C12M 47/04 |
| 2014/0363891 A1* | 12/2014 | Llull | A61K 45/06 |
| | | | 435/378 |

FOREIGN PATENT DOCUMENTS

| | | |
|---|---|---|
| CN | 207727059 U | 8/2018 |
| CN | 109700488 A | 5/2019 |
| CN | 110523491 A | 12/2019 |
| CN | 110560232 A | 12/2019 |
| CN | 210675409 U | 6/2020 |
| TW | 201512395 A | 4/2015 |

* cited by examiner

US 11,305,051 B2

FAT CUTTER AND INTEGRATED MACHINE FOR PREPARATION OF IN VITRO FINE-PARTICLE FAT

CROSS REFERENCE TO THE RELATED APPLICATIONS

This application is the national phase entry of International Application No. PCT/CN2020/072819, filed on Jan. 17, 2020, which is based upon and claims priority to Chinese Patent Applications No. 201910942443.5 and No. 201910942409.8, filed on Sep. 30, 2019, the entire contents of which are incorporated herein by reference.

TECHNICAL FIELD

The present invention relates to a fat cutter and an integrated machine for preparation of in vitro fine-particle fat.

BACKGROUND

Due to a plurality of advantages such as abundant sources, convenient material acquisition, no rejection, simple operation, good filled appearance, no disease infection, and no postoperative scars, autologous fat has been widely used in clinics, and has become a common means for tissue filling and wound repair in plastic surgery. However, the graft survival rate, especially the uncertainty of long-term survival, is still the main obstacle that restricts application of the autologous fat. Improving the survival rate, especially, the long-term survival rate, of fat after grafting, is still a problem that needs to be resolved urgently. A large number of studies show that the volume of grafted adipose tissue can still only retain 50%-80% at present.

Studies show that in an early stage of grafting, adipose tissue is in a state of ischemia and hypoxia and relies on nutrients provided by surrounding interstitial fluid, adipocytes survive well within 1.5±0.5 mm from interstitial fluid of a recipient site, and neovascularization starts around the graft 5 days after surgery, but if the diameters of fat particles are greater than 2 mm, limited by a distance of interstitial fluid dispersion, adipocytes in the center of the fat particles are liquefied and necrotic because of being restricted from receiving nutrients and oxygen. Therefore, nutrition and timely establishment of a blood supply of the grafted fat in the recipient site in the early stage largely depend on the diameters of fat particles.

In 2001, Zuk et al. found mesenchymal stem cells (MSCs), referred to as adipose-derived stem cells (ADSCs), in adipose tissue for the first time. Like bone marrow-derived MSCs, the ADSCs also have good potential of self-renewal and multi-directional differentiation. However, adipose stem cells are more convenient to obtain and cause less pain. More importantly, the content of stem cells in adipose tissue is 500 to 1000 times that in bone marrow. In a process of fat grafting, the ADSCs can, on the one hand, increase the density of blood vessels in free grafted adipose tissue to help the graft to establish a timely and adequate blood supply in an early stage, and can, on the other hand, differentiate into adipocytes to supplement a reduced number of adipocytes, thereby effectively improving the survival rate of the grafted fat, and increasing the content of the ADSCs in the grafted fat.

Fat particles obtained by using a large-diameter (which refers to the diameter of which $\varphi \geq 4$ mm and the cross-sectional area S of a lateral hole $\geq 10$ mm$^2$) liposuction cannula are large, but a distance of interstitial fluid dispersion is limited. Consequently, adipocytes are necrotic due to poor blood supply. Therefore, it is clinically recognized that small-diameter ($\varphi=2$ mm and S=1 mm$^2$), low-negative pressure liposuction is the key to successful fat grafting. A large-diameter liposuction tube is not recommended for liposuction. Although suctioning fat by using a small-diameter liposuction tube has many advantages, the content of ADSCs in suctioned fat particles is low, which may be due to the factor that ADSCs are mainly distributed around interstitial blood vessels and fascia (connective tissue) of adipose tissue. Because the blood vessels and fascia are relatively dense and tough, the content of ADSCs in fat obtained by the small-diameter liposuction tube is significantly lower than the content of ADSCs in a donor site, and the ADSCs lack an extracellular matrix (including fascia, interstitial blood vessels, and the like). Even if the extracellular matrix is obtained, the extracellular matrix is easy to form a reticular mass due to characteristics thereof, resulting in a relatively large volume and difficulty in injection.

The patent application No. 201910125174.3, entitled "INTEGRATED MACHINE FOR PREPARATION of IN VITRO FINE-PARTICLE FAT", discloses a device that suctions fat by using a large-diameter liposuction tube and further cut fat by using a fat cutting device. This device has high liposuction efficiency and a high survival rate of grafted fat, and can resolve the foregoing technical problems. However, it is found through further researches on this device that a cutting effect of the cutting part of the device is unstable, fat particles after cutting have different sizes, the fat after cutting is easy to splash, resulting in a fat loss, and the collection part of the device is inconvenient to disassemble, maintain, and sterilize, resulting in a possibility of bacterial contamination of fat.

Technical Problem

The patent application No. 201910125174.3, entitled "INTEGRATED MACHINE FOR PREPARATION of IN VITRO FINE-PARTICLE FAT", discloses a device that suctions fat by using a large-diameter liposuction tube and further cut fat by using a fat cutting device. This device has high liposuction efficiency and a high survival rate of grafted fat, and can resolve the foregoing technical problems. However, it is found through further researches on this device that a cutting effect of the cutting part of the device is unstable, fat particles after cutting have different sizes, the fat after cutting is easy to splash, resulting in a fat loss, and the collection part of the device is inconvenient to disassemble, maintain, and sterilize, resulting in a possibility of bacterial contamination of fat.

SUMMARY

A fat cutter is provided, including a fat inlet channel, a fat outlet channel, at least one set of blades disposed between an outlet of the fat inlet channel and an inlet of the fat outlet channel, and a housing that seals a space in which the outlet of the fat inlet channel, the inlet of the fat outlet channel, and the blades are located, where a fat inlet of the fat inlet channel is connected to a large-diameter liposuction tube, and a fat outlet of the fat outlet channel is connected to a high-negative pressure device; and the outlet of the fat inlet channel and the inlet of the fat outlet channel are oppositely provided, and a gap is provided therebetween to form a cutting slot matching the thickness of the blades, the outlet of the fat inlet channel is provided above the inlet of the fat outlet channel, and in a working state, cutting edges of the blades pass through a line connecting the outlet of the fat inlet channel and the inlet of the fat outlet channel to cut fat particles. By using the foregoing structure, in a process in which under the traction of negative pressure, fat enters the fat inlet channel through the large-diameter liposuction tube, then flows out from the outlet of the fat inlet channel, and is about to fall into the inlet of the fat outlet channel, the fat is cut into smaller particles by using high-speed rotating blades, and the small-particle fat after cutting is suctioned out from this device under the traction of negative pressure. Because the gap between the fat inlet channel and the fat outlet channel is small, and the negative pressure in the channel after the gap is greater than the negative pressure in the gap in magnitude, on the one hand, the fat particles lack the force to leave the channels, so that the fat particles after cutting are directly drawn into the fat outlet channel by the negative pressure, to minimize the fat particles remaining inside the device, and on the other hand, it can be ensured that the fat particles after cutting are free from being cut a plurality of times, thereby reducing damage to the fat particles. The diameters of the fat particles after cutting can be adjusted appropriately by controlling the rotational speed of the blades to meet different requirements. The device can be used for fat grafting and pure liposuction. During pure liposuction, the device is directly connected to a negative pressure tank. During fat grafting, a negative pressure generator is connected to a fat collection tank and is further connected to the device. Therefore, this device can have a plurality of applications.

In the foregoing implementation, the housing includes a cutting table and an upper end cover mounted above the cutting table, a fat particle cutting device that drives the set of blades is mounted in the cutting table, the fat inlet channel is provided on the upper end cover, the fat outlet channel is provided at a position of the cutting table corresponding to the fat inlet channel, the upper end cover is sealed and mounted on the cutting table by using a seal, and in an assembled state, the gap is provided in a region in which the outlet of the fat inlet channel and the inlet of the fat outlet channel are located and between the upper end cover and the cutting table to form an annular cutting slot, and the set of blades of the fat particle cutting device is disposed in the cutting slot. The upper end cover is sealed on the cutting table to form the cutting slot, so that the entire structure is convenient to disassemble and maintain. All parts of this device are made of food-grade stainless steel or polymer materials, so that this device is convenient to sterilize at a high temperature and a high pressure.

In the foregoing implementation, the outlet of the fat inlet channel is coaxially provided above the inlet of the fat outlet channel, a projection of the outlet of the fat inlet channel on a horizontal plane falls within a range of a projection of the inlet of the fat outlet channel on the horizontal plane, and an axis of the fat inlet channel and the fat outlet channel is parallel to a rotation axis of the blades. In this way, under the action of negative pressure, the fat falling from the fat inlet channel can accurately fall into the fat outlet channel, thereby preventing a fat loss.

In the foregoing implementation, the cutting edges and blade faces of the blades are perpendicular to the axis of the fat inlet channel and the fat outlet channel, to ensure the cutting effect and prevent splashing during cutting.

In the foregoing implementation, the height of the cutting slot is 2-4 mm. The height matches the thickness of the blades, which on the one hand, ensures the effect of negative pressure, and on the other hand, prevents the rotating blades from interfering with a wall of the cutting slot.

In the foregoing implementation, an inner side of a periphery of the upper end cover is connected to an outer side of a periphery of the cutting table in a sealed manner by an O-shaped sealing ring.

In the foregoing implementation, quick connectors are disposed on the fat inlet of the fat inlet channel and the fat outlet of the fat outlet channel, to facilitate quick connection and disassembly between the channels and this device.

In the foregoing implementation, the fat particle cutting device includes the blades, a blade carrier, a shaft, and a speed-regulating motor, the blades are mounted on the blade carrier, the blades and the blade carrier are fixed on the shaft by a self-locking nut, the shaft is mounted on the cutting table through a bearing, the bearing and the cutting table, and the shaft and the cutting table are respectively sealed by a sealing ring, and the shaft is connected to the speed-regulating motor by a buffer coupling.

In the foregoing implementation, the speed-regulating motor is electrically connected to a controller, and the controller includes a rotational speed display screen for displaying a rotational speed of the speed-regulating motor, a speed-regulating switch for regulating the rotational speed of the speed-regulating motor, a work indicator for displaying a state of the speed-regulating motor, and a power switch for controlling on and off of the speed-regulating motor.

In the foregoing implementation, the rotational speed of the blades is adjustable within a range of 0-4000 rpm, preferably 2500-3000 rpm. It is ensured, through a large number of experiments, that the diameters of most of the fat particles cut by the blades at the rotational speed are less than or equal to 2 mm, to effectively avoid central necrosis of the grafted fat caused by excessively large particles.

In the foregoing implementation, the liposuction tube has a length of 25-40 cm and a diameter of 4-5 mm. A liposuction end of the liposuction tube is provided with 4-6 lateral holes, and the cross-sectional area of each side hole is 20-30 $mm^2$. The liposuction tube that adopts this specification meets the requirements for a large diameter and a high negative pressure.

In the foregoing implementation, the liposuction tube includes a handle and a liposuction cannula, a liposuction channel and an air bleed channel are provided in the handle, an air guide channel is further provided on the housing, the air guide channel is in communication with the cutting slot, an outlet of the liposuction channel is connected to the fat inlet of the fat inlet channel of the housing by a liposuction pipeline, a connection channel is further provided in the handle, an air bleed hole is provided on an outer side of the handle, a front end of the air bleed channel is in communication with the connection channel, one end of the connection channel is in communication with the air bleed hole provided on the handle, an other end is in communication with the liposuction channel, an angle is formed between the connection channel and the liposuction channel to prevent suctioned fat from entering the connection channel from the liposuction channel, and an outlet end of the air bleed channel is connected to an air inlet of the air guide channel of the housing by an air bleed tube. The air bleed channel is added in the liposuction handle. An operator presses the air bleed hole with a finger to open and close the air bleed hole and adjust an opening size of the air bleed hole. When the air bleed hole of the air bleed channel is opened, the cutting slot is in communication with the outside through the air bleed channel, so that the negative pressure in the cutting slot is reduced, and a force for suctioning fat is reduced, thereby reducing splashing of fat and reducing fat damage.

In the foregoing implementation, the angle between the connection channel and the liposuction channel facing a connector of the liposuction cannula is an acute angle, to prevent suctioned fat from entering the connection channel from the liposuction channel.

In the foregoing implementation, a groove that helps to press and seal the air bleed hole with pulp of a thumb is provided in a region of the handle in which the air bleed hole is located, so that the air bleed hole can be conveniently sealed and adjusted in size through the contact between the pulp of the thumb and the groove.

In the foregoing implementation, an inner wall of the cutting slot and an inner wall of the inlet of the fat outlet channel are both covered with a soft material layer, to reduce damage after fat hits the inner walls.

In the foregoing implementation, the inlet of the fat outlet channel is smaller than an outlet of the cutting slot to form a step, and an inner wall of the step, a joint between the step and the outlet of the cutting slot, and a joint between the step and the inlet of the fat outlet channel are all curved surfaces, so that fat after cutting moves forward and downward due to inertia and directly falls onto the curved surfaces to be quickly suctioned away, to be free from being cut a second time or a plurality of times due to impact and bounce.

An implementation of the present invention further includes an integrated machine for preparation of in vitro fine-particle fat, including the foregoing fat cutter, and further including a fat collection tank, a negative pressure generator, and a negative pressure tank set, where the fat collection tank includes a cylinder and a filter cartridge, a top portion of the cylinder is provided with an opening, a bottom portion of the cylinder is provided with a negative pressure interface in communication with an inner cavity of the cylinder, the filter cartridge is formed by a strainer of which the diameters of filter holes are less than those of to-be-filtered fat particles, after the filter cartridge is mounted in the cylinder, there is a gap between a periphery of the filter cartridge and an inner wall of the cylinder and there is a gap between a bottom portion of the filter cartridge and an inner wall of the cylinder, a top portion of the filter cartridge is provided with an opening, an end cover is sealed and mounted on the opening of the filter cartridge, the end cover is connected to the cylinder in a sealed manner after the filter cartridge is mounted in the cylinder, an inlet-outlet is provided on the end cover, the fat outlet of the fat outlet channel on the fat cutter is connected to the inlet-outlet of the fat collection tank by a connection pipeline, the negative pressure generator is connected to the negative pressure tank set by a pipeline, and the negative pressure tank set is connected to the negative pressure interface of the fat collection tank by a pipeline.

In the foregoing implementation, a self-locking buckle is disposed on an outer wall of the cylinder, a gasket is disposed on the end cover, and after the filter cartridge is mounted in the cylinder, the end cover is connected to an opening edge of the cylinder by the gasket, and the end cover is tightly pressed on the opening edge of the cylinder through the self-locking buckle on the cylinder, so that the end cover and the cylinder are sealed.

In the foregoing implementation, the fat cutter, the negative pressure generator, and the negative pressure tank set are mounted on a support, and a plurality of casters for support are mounted at a bottom portion of the support.

In the foregoing implementation, the filter cartridge includes a lower strainer and an upper closed cone, and the height of the strainer is ⅓-¾ of the height of the entire filter cartridge. In this way, when the suctioned fat exceeds the part of the strainer, a pressure difference is generated between an upper end of the fat and the collection tank, so that water can be better drawn away to reduce the water content during fat injection so as to prevent the excessively large water content from affecting determining of an injection volume.

Beneficial Effects of the Invention

The fat cutter in the foregoing implementations changes the inherent clinical thinking "a small-diameter, low-negative pressure liposuction tube is necessary for liposuction in fat grafting", and resolves problems currently faced by fat grafting. In a process in which under traction of negative pressure, fat enters the fat inlet channel through the large-diameter liposuction tube, then flows out from the outlet of the fat inlet channel, and is about to fall into the inlet of the fat outlet channel, the fat is cut into smaller particles by using high-speed rotating blades, and the small-particle fat after cutting is suctioned out from this device under the traction of negative pressure. Because the gap between the fat inlet channel and the fat outlet channel is small, and the negative pressure in the channel after the gap is greater than the negative pressure in the gap in magnitude, on the one hand, the fat particles lack the force to leave the channels, so that the fat particles after cutting are directly drawn into the fat outlet channel by the negative pressure, to minimize the fat particles remaining inside the device, and on the other hand, it can be ensured that the fat particles after cutting are free from being cut a plurality of times, thereby reducing damage to the fat particles.

The integrated machine for preparation of in vitro fine-particle fat in the foregoing implementations further improves a large diameter, high-negative pressure integrated machine for preparation, so that if the same volume of particle fat is suctioned, the content of the ADSCs is 1.7 to 3 times higher than that in an existing preparation method, and more injectable extracellular matrices can be obtained. The integrated machine for preparation of in vitro fine-particle fat cuts and crushes the fat suctioned by the large-diameter liposuction tube in vitro to change large-particle fat into small-particle fat, which not only resolves the problem of adipocyte necrosis caused by excessively large fat particles, but also resolves the problems of a low content of ADSCs and lack of an extracellular matrix in the obtained adipose tissue while ensuring cell activity. It is also found through experiments that clinical liposuction efficiency can be significantly improved (by up to 3 to 5 times) by using a large-diameter liposuction tube.

Based on the above, the present invention resolves the problems, such as time-consuming and laborious liposuction, a low content of ADSCs, lack of an extracellular matrix, and vulnerability to contamination in a purification process, during fat grafting, and the entire system can also be connected to a liposuction machine to become a device for liposuction and body sculpting.

Figure 1:
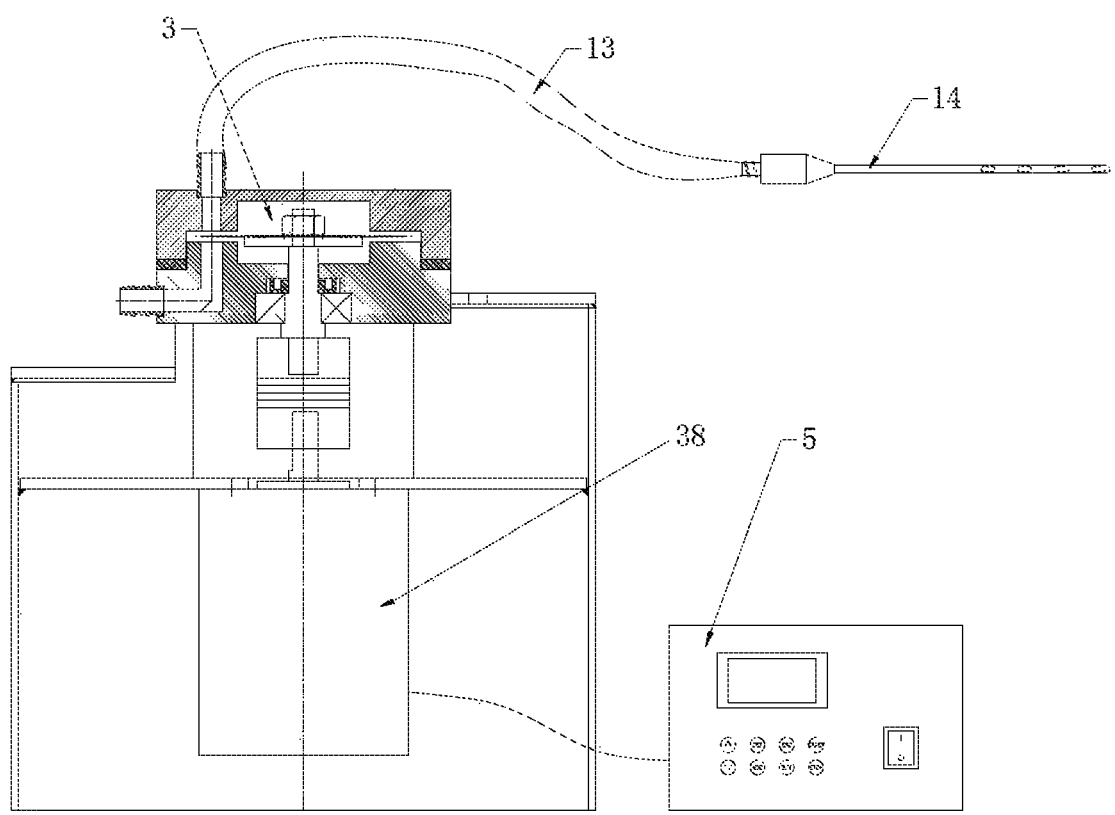
FIG. 1 is a schematic structural diagram of a fat cutter in Embodiment 1.
Figure 2:
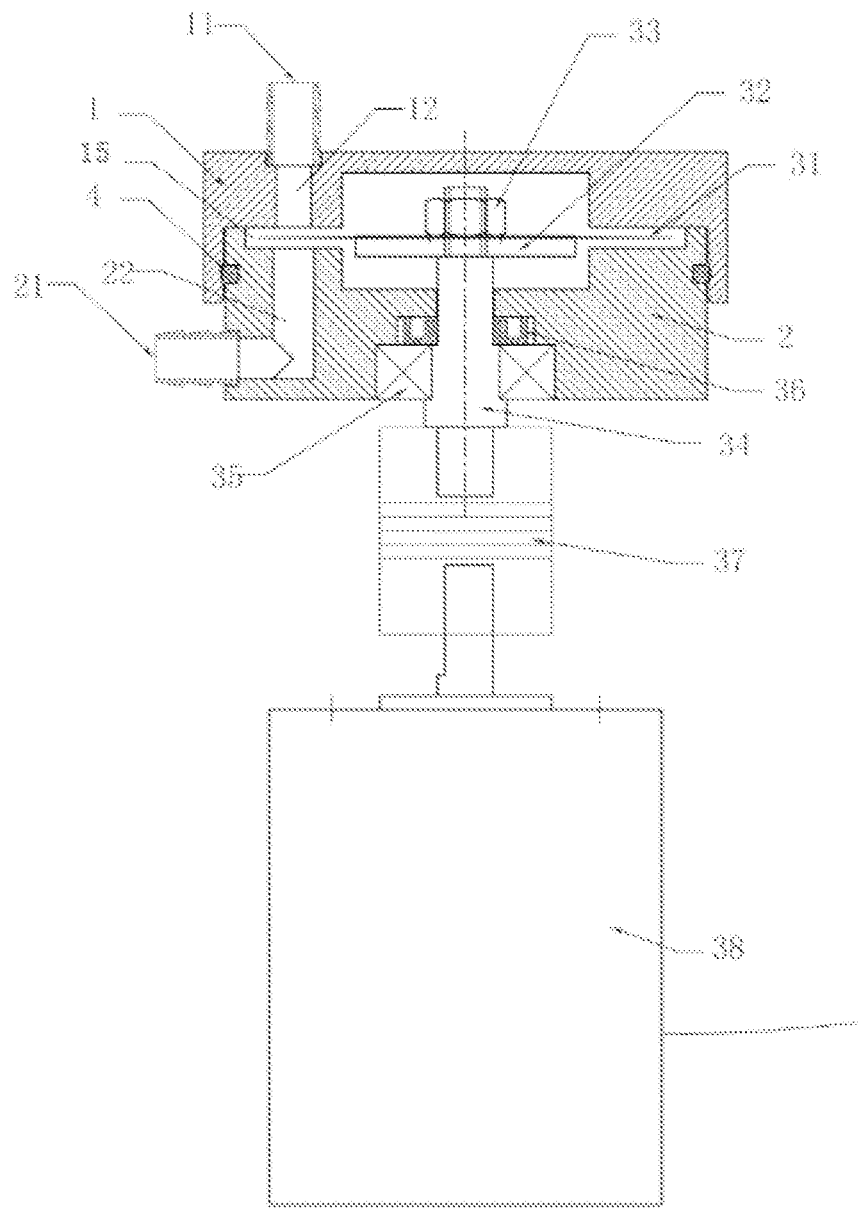
FIG. 2 is a schematic structural diagram of an upper end cover and a cutting table of a fat cutter in Embodiment 1.
Figure 3:
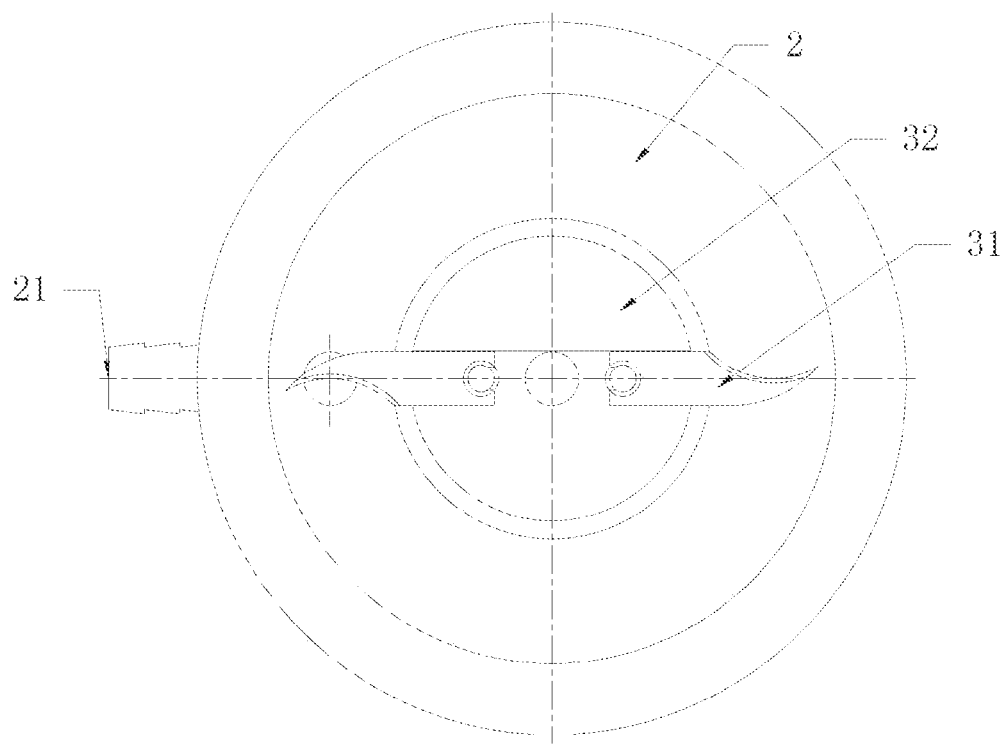
FIG. 3 is a top view of a cutting table of a fat cutter in Embodiment 1.
Figure 4:
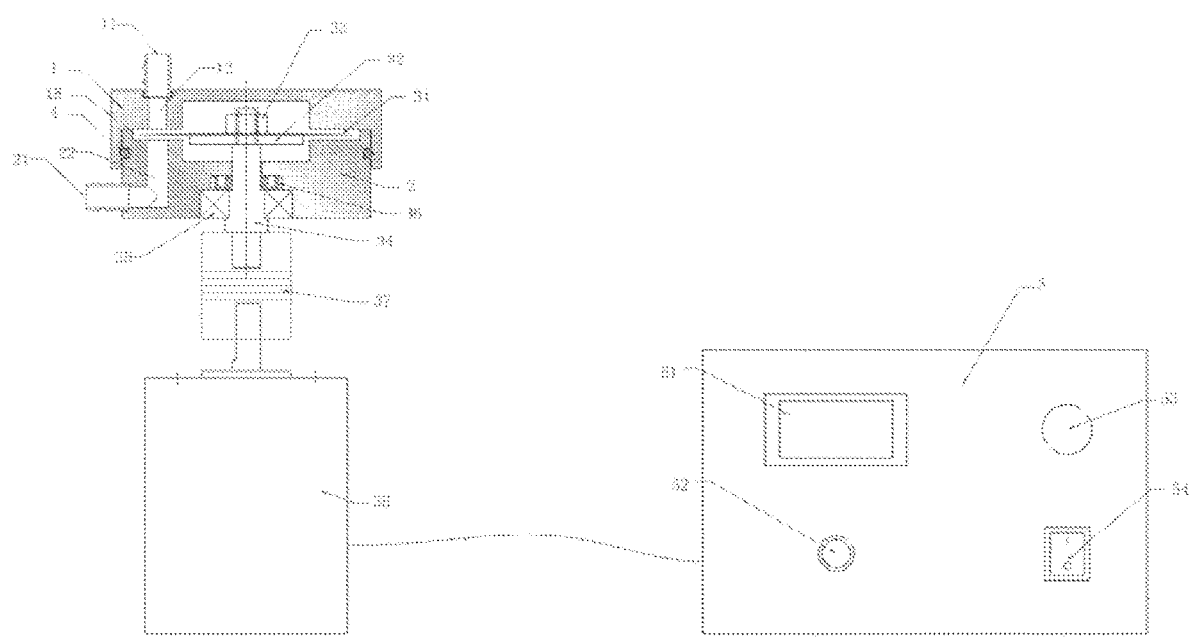
FIG. 4 is a schematic structural diagram of a fat cutter in Embodiment 1 after a cutting table is connected to a controller.

In the drawings: 1. Upper end cover, 11. Fat inlet, 12. Fat inlet channel, 13. Liposuction pipeline, 14. Liposuction tube, 141. Handle, 1411. Air bleed channel, 1412. Liposuction channel, 1413. Connection channel, 1414. Air bleed hole, 1415. Groove, 142. Liposuction cannula, 15. Cutting slot, 16. Step, 17. Air inlet, 18. Air guide channel, 19. Air bleed tube, 2. Cutting table, 21. Fat outlet, 22. Fat outlet channel, 3. Cutting device, 31. Blade, 32. Blade carrier, 33. Self-locking nut, 34. Shaft, 35. Bearing, 36. Sealing ring, 37. Buffer coupling, 38. Speed-regulating motor, 4. O-shaped sealing ring, 5. Controller, 51. Rotational speed display screen, 52. Speed-regulating switch, 53. Work indicator, 54. Power switch, 6. Collection tank, 61. End cover, 62. Cylinder, 63. Filter cartridge, 64. Flow guide port, 65. Self-locking buckle, 66. Opening edge, 67. Gasket, 68. Inlet-outlet, 69. Negative pressure interface, 7. Fixed frame, 8. Connection pipeline, 9. Support, 91. Caster, 92. Negative pressure tank, 93. Quick connector, and 94. Negative pressure generator.

DETAILED DESCRIPTION OF THE EMBODIMENTS

Embodiment 1

As shown in FIG. 1 to FIG. 4, a fat cutter includes a cutting table 2 and an upper end cover 1 mounted above the cutting table 2. A fat particle cutting device 3 for driving blades 31 to rotate is mounted in the cutting table 2. A fat inlet channel 12 is provided on the upper end cover 1. A fat outlet channel 22 is provided at a position of the cutting table 2 corresponding to the fat inlet channel 12. A fat inlet 11 of the fat inlet channel 12 is connected to a large-diameter liposuction tube 14 by a liposuction pipeline 13 (the large-diameter liposuction tube 14 means that φ of a liposuction channel ≥4 mm and the cross-sectional area S of each lateral hole of the liposuction cannula ≥10 mm$^2$). The liposuction tube 14 has a length of 25-40 cm and a diameter of 4-5 mm, the liposuction cannula of the liposuction tube 14 is provided with 4-6 lateral holes, and the cross-sectional area of each lateral hole is 20-30 mm$^2$. A fat outlet 21 of the fat outlet channel 22 is connected to a high-negative pressure device, and a recommended range of negative pressure provided by the high-negative pressure device is 0.06-0.08 MPa. An outlet of the fat inlet channel 12 and an inlet of the fat outlet channel 22 are oppositely provided, and a gap therebetween matches the thickness of the blades. The outlet of the fat inlet channel 12 is provided above the inlet of the fat outlet channel 22, and further, the outlet of the fat inlet channel 12 is coaxially provided above the inlet of the fat outlet channel 22, and a projection of the outlet of the fat inlet channel 12 on a horizontal plane falls within a range of a projection of the inlet of the fat outlet channel 22 on the horizontal plane, so that fat falls directly from the outlet of the fat inlet channel 12 into the inlet of the fat outlet channel 22 without spilling. An axis of the fat inlet channel 12 and the fat outlet channel 22 is parallel to a rotation axis of the blades 31 to ensure that cutting edges of the blades are perpendicular to the axis for a cutting effect.

The fat particle cutting device 3 includes the blades 31, a blade carrier 32, a shaft, and a speed-regulating motor 38. The blades 31 are mounted on the blade carrier 32, and the blades 31 and the blade carrier 32 are fixed on the shaft by a self-locking nut 33. The shaft is mounted on the cutting table 2 through a bearing 35 and is disposed coaxially with a central axis of the cutting table. The bearing 35 and the cutting table 2, and the shaft and the cutting table 2 are respectively sealed by a sealing ring 36. The shaft is connected to the speed-regulating motor 38 by a buffer coupling 37.

The speed-regulating motor 38 is electrically connected to a controller 5. The controller 5 includes a rotational speed display screen 51 for displaying a rotational speed of the speed-regulating motor 38, a speed-regulating switch 52 for regulating the rotational speed of the speed-regulating motor 38, a work indicator 53 for displaying a state of the speed-regulating motor 38, and a power switch 54 for controlling on and off of the speed-regulating motor 38.

An O-shaped sealing ring 4 is mounted inside a fixed side of the upper end cover 1. The upper end cover 1 is connected to the cutting table 2 in a sealed manner by the O-shaped sealing ring 4. After the upper end cover 1 is mounted on the cutting table 2, the gap is provided in a region in which the outlet of the fat inlet channel 12 and the inlet of the fat outlet channel 22 are located and between the upper end cover 1 and the cutting table 2 to form an annular cutting slot 15. The blades 31 of the fat particle cutting device 3 are disposed in the cutting slot 15. In this embodiment, the height of the cutting slot 15 is 2-4 mm, to accommodate at least the height of one blade. The blades are kept at a rotational speed of 2500-3000 rpm. The height of the cutting slot 15 prevents the blades from interfering with the cutting slot 15 during high-speed rotation. The foregoing structure causes the diameters of the fat particles obtained through cutting to be less than or equal to 2 mm, to effectively avoid central necrosis of the grafted fat caused by excessively large particles.

In another implementation of this device, a set of blades 31 is disposed between the outlet of the fat inlet channel 12 and the inlet of the fat outlet channel 22, and neighboring blades 31 are arranged along a line connecting the outlet of the fat inlet channel 12 and the inlet of the fat outlet channel 22. When entering the cutting slot 15, fat is cut by high-speed rotating blades and quickly suctioned out, to be free from being cut a plurality of times, thereby reducing damage to the fat particles.

In this embodiment, quick connectors 93 are disposed on the fat inlet 11 of the fat inlet channel 12 and the fat outlet 21 of the fat outlet channel 22, to facilitate quick connection and disassembly between the channels and this device.

In this embodiment, the high negative pressure can be achieved by using a hospital negative-pressure suction system or by independently configuring a negative pressure generator and a negative pressure tank.

When this embodiment is used in fat preparation, a negative pressure system is connected to a fat outlet of this device. In a process in which under the traction of negative pressure, fat enters the fat inlet channel 12 through the large-diameter liposuction tube, then enters the cutting slot 15 from the outlet of the fat inlet channel 12, and is about to fall into the inlet of the fat outlet channel 22, the fat is cut into smaller particles by using high-speed rotating blades of the fat particle cutting device 3, and the small-particle fat after cutting is suctioned out from this device under the traction of negative pressure. In this way, the fat cutting is completed.

Embodiment 2

Figure 5:
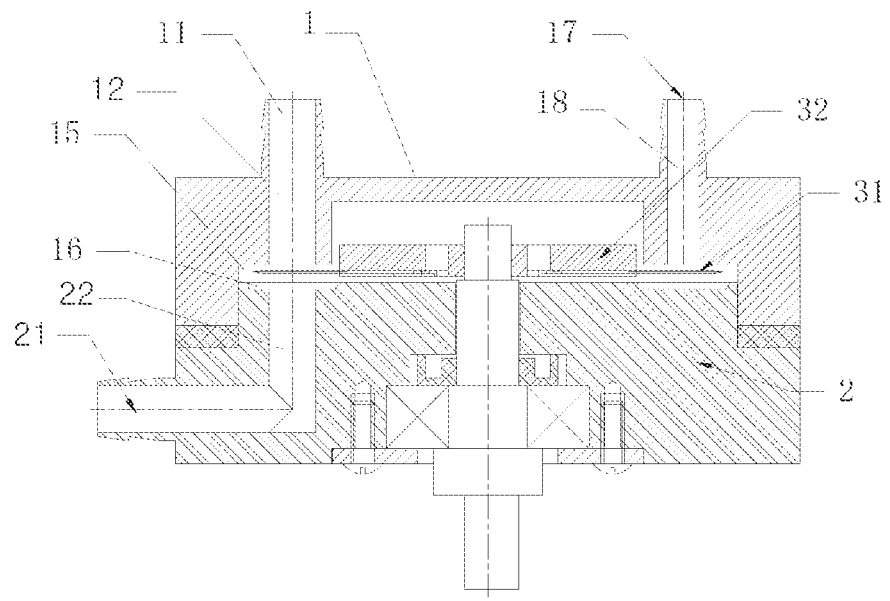
FIG. 5 is a schematic structural diagram of a fat cutter in Embodiment 2.
Figure 6:
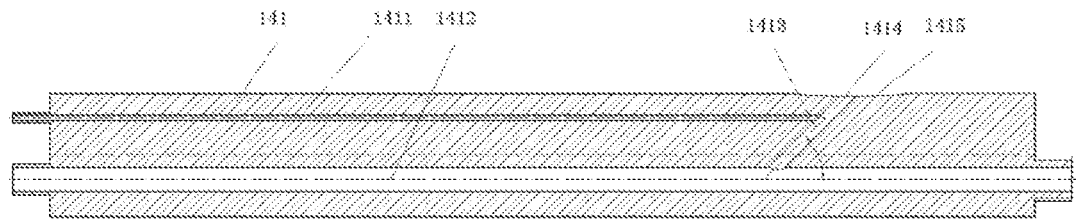
FIG. 6 is a cross-sectional view of a liposuction tube of a fat cutter in Embodiment 2.
Figure 7:
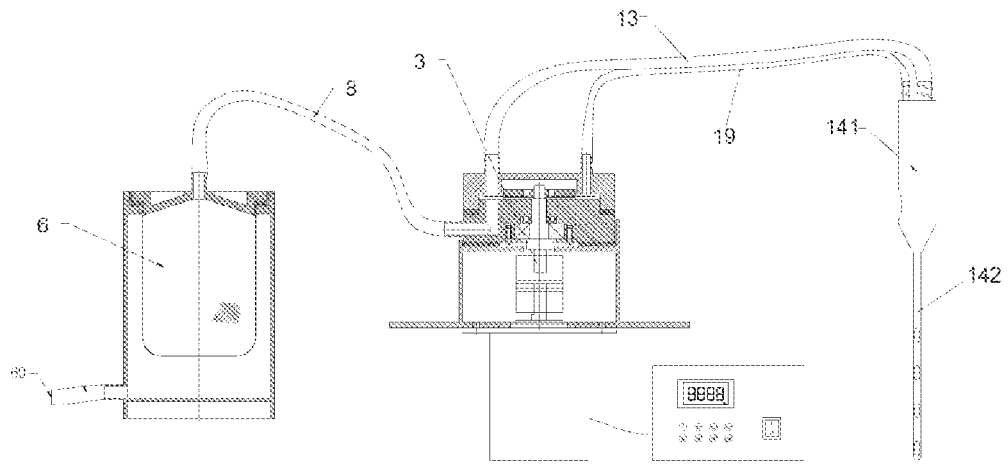
FIG. 7 is a schematic structural diagram of a fat cutter connected to a liposuction tube in Embodiment 2.

As shown in FIG. 5 to FIG. 7, for a fat cutter, Embodiment 1 differs from Embodiment 2 in that: The liposuction tube 14 includes a handle 141 and a liposuction cannula 142. A liposuction channel 1412 and an air bleed channel 1411 are provided in the handle 141. The liposuction cannula 142 is mounted on an inlet of the liposuction channel 1412. An air guide channel 18 in communication with the cutting slot 15 is further provided on the upper end cover 1. A connection channel 1413 is further provided in the handle 141. An air bleed hole 1414 is provided on an outer side of the handle 141. A front end of the air bleed channel 1411 is in communication with a middle portion of the connection channel 1413. One end of the connection channel 1413 is in communication with the air bleed hole 1414 provided on the handle 141, and an other end is in communication with a middle portion of the liposuction channel 1412. An angle is formed between the connection channel 1413 and the liposuction channel 1412 to prevent fat from entering the connection channel 1413 from the liposuction channel 1412. An outlet end of the air bleed channel 1411 is connected to an air inlet of the air guide channel of the housing by an air bleed tube 19.

In this embodiment, a connector of the liposuction cannula 142 is disposed on an inlet end of the liposuction channel 1412 of the handle 141, a connector of the liposuction pipeline 13 is disposed on an outlet end of the liposuction channel 1412 of the handle 141, and a connector of the air bleed tube 19 is disposed on an outlet end of the air bleed channel 1411. The angle between the connection channel 1413 and the liposuction channel 1412 facing the connector of the liposuction cannula 142 is an acute angle, preferably 45 degrees. The connector of the liposuction cannula 142, the connector of the liposuction pipeline 13, and the connector of the air bleed tube 19 are quick connectors.

In this embodiment, a groove 1415 that helps to press and seal the air bleed hole 1414 with pulp of a thumb is provided in a region of the handle 141 in which the air bleed hole 1414 is located, an inner wall of the cutting slot 15 and an inner wall of the inlet of the fat outlet channel 22 are both covered with a soft material layer, and an inner wall of the step 16, a joint between the step 16 and an outlet of the cutting slot 15, and a joint between the step 16 and the inlet of the fat outlet channel 22 are all curved surfaces.

Embodiment 3

Figure 8:
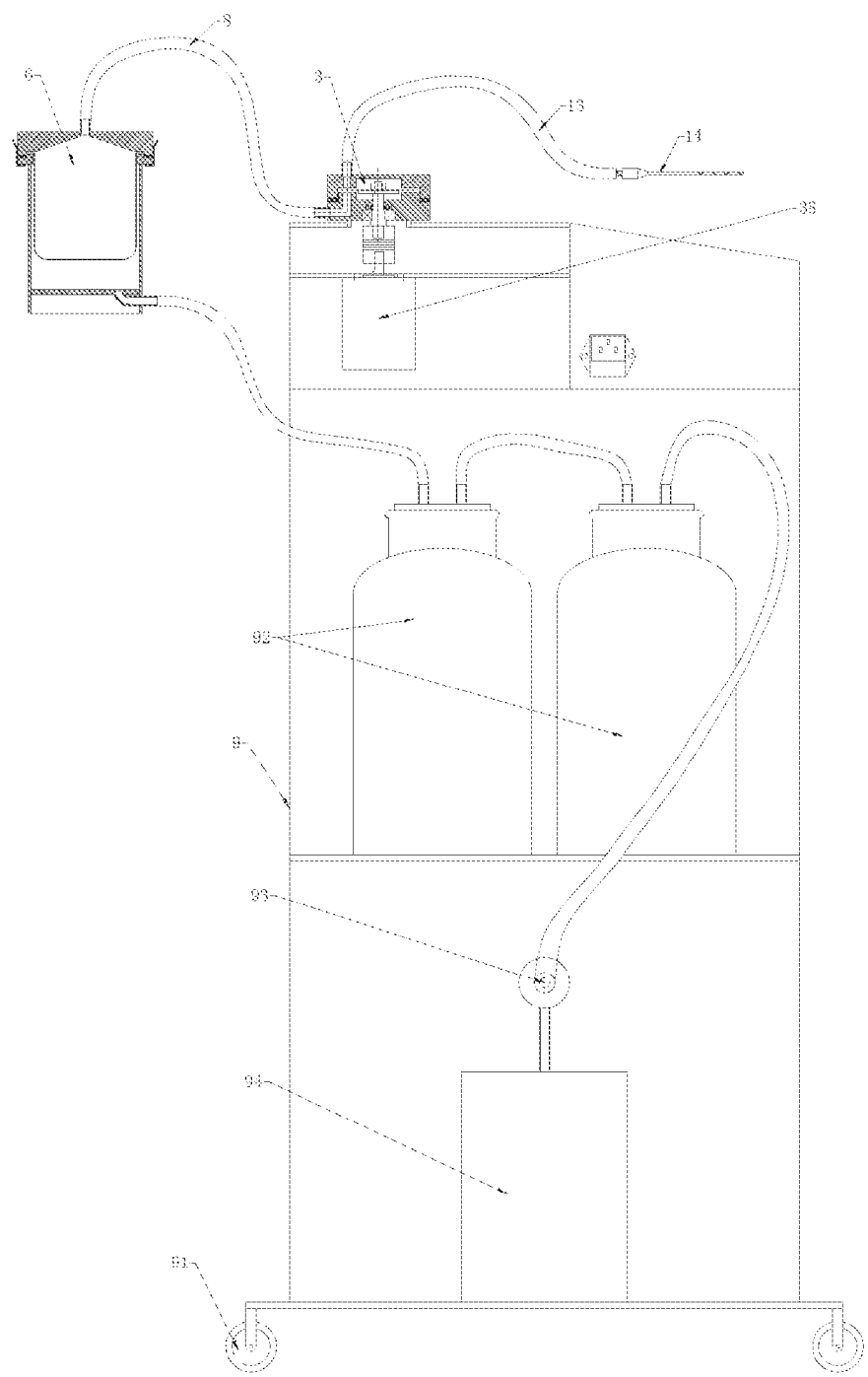
FIG. 8 is a schematic diagram of an overall structure of an integrated machine for preparation of in vitro fine-particle fat in Embodiment 3.
Figure 9:
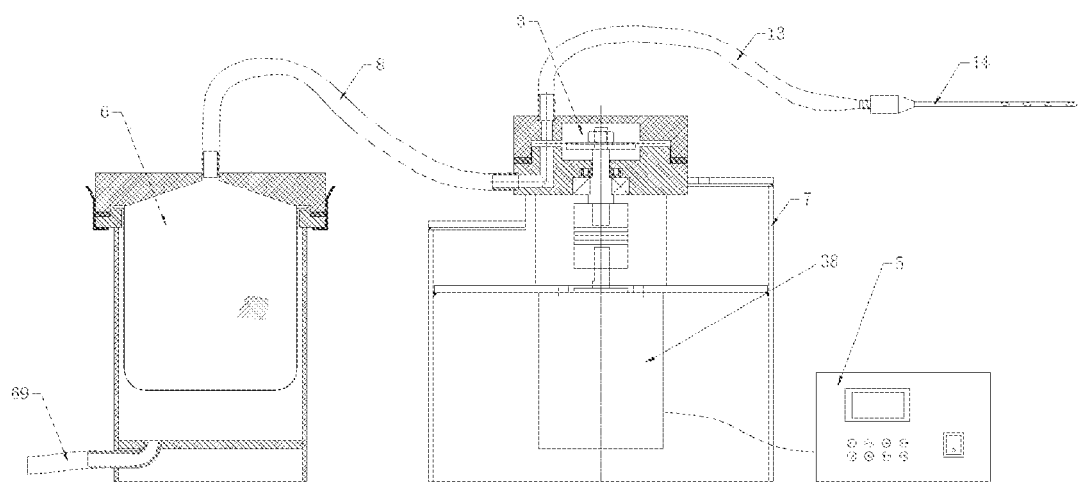
FIG. 9 is a schematic structural diagram of an integrated machine for preparation of in vitro fine-particle fat in Embodiment 3 after a fat cutter is connected to a fat collection tank.
Figure 10:
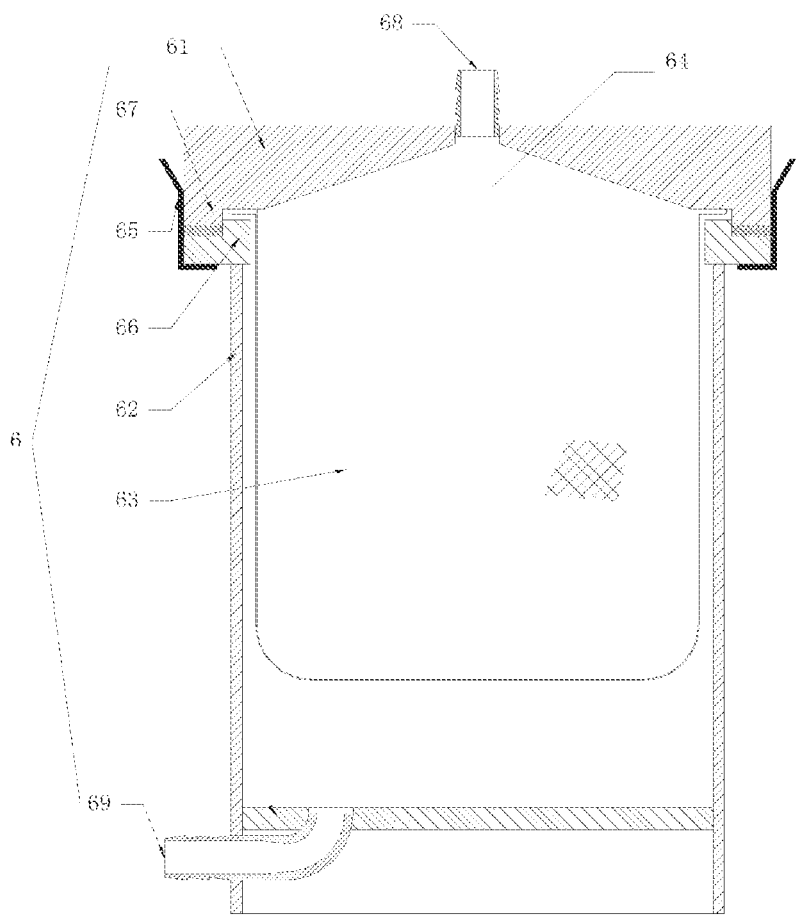
FIG. 10 is a cross-sectional view of a fat collection tank of an integrated machine for preparation of in vitro fine-particle fat in Embodiment 3.

As shown in FIG. 8 to FIG. 10, an integrated machine for preparation of in vitro fine-particle fat includes a fat collection tank 6, a support 9, a fat cutter mounted on the support, a negative pressure generator 94, and a negative pressure tank set 92. The fat cutter is mounted on the support 9 through a fixed frame 7. The fat cutter includes the fat cutters in Embodiment 1 and Embodiment 2.

As shown in FIG. 10, the fat collection tank 6 includes a cylinder 62 and a filter cartridge 63. A top portion of the cylinder 62 is provided with an opening. A bottom portion of the cylinder 62 is provided with a negative pressure interface 69 in communication with an inner cavity of the cylinder 62. The filter cartridge 63 is formed by a strainer of which the diameters of filter holes are less than those of to-be-filtered fat particles. After the filter cartridge 63 is mounted in the cylinder 62, there is a gap between a periphery of the filter cartridge 63 and an inner wall of the cylinder 62 and there is a gap between a bottom portion of the filter cartridge 63 and an inner wall of the cylinder 62. A top portion of the filter cartridge 63 is provided with an opening. An end cover 61 is sealed and mounted on the opening of the filter cartridge 63. A conical flow guide port 64 of which the diameter of a bottom surface matches the diameter of the filter cartridge 63 is formed on an inclined surface that has an inlet-outlet 68 as a center of inclination and that is provided on a side of the end cover 61 that is disposed inside the filter cartridge 63. In this embodiment, the diameter of the inlet-outlet is about 4-6 mm. The design of the flow guide port on the end cover allows fat to be guided out through the flow guide port when the fat is taken out, thereby avoiding a loss caused by that the fat is stuck in a corner and cannot flow out during the guiding out. The fat outlet 21 of the fat outlet channel 22 is connected to the inlet-outlet 68 of the fat collection tank 6 by a connection pipeline 8. The negative pressure generator 94 is connected to the negative pressure tank set 92 by a pipeline. The negative pressure tank set 92 is connected to the negative pressure interface 69 of the fat collection tank 6 by a pipeline. A quick connector 93 is disposed on an end of the negative pressure tank set 92 for connecting the fat collection tank 6. The negative pressure generator 94 provides negative pressure, so that the negative pressure at a liposuction end of the liposuction tube 14 ranges from 0.06 to 0.08 MPa.

In another implementation of the fat collection tank, the filter cartridge 63 includes a lower strainer and an upper closed cone, and the height of the strainer is ⅓-¾ of the height of the entire filter cartridge. In this way, when the suctioned fat exceeds the part of the strainer, a pressure difference is generated between an upper end of the fat and the collection tank, to reduce the water content during fat injection so as to prevent the excessively large water content from affecting determining of an injection volume.

A self-locking buckle 65 is disposed on an outer wall of the cylinder 62. A gasket 67 is disposed on the end cover 61. After the filter cartridge 63 is mounted in the cylinder 62, the end cover 61 is connected to an opening edge 66 of the cylinder 62 by the gasket 67, and the end cover 61 is tightly pressed on the opening edge 66 of the cylinder 62 through the self-locking buckle 65 on the cylinder 62, so that the end cover 61 and the cylinder 62 are sealed. The inlet-outlet 68 is provided on the end cover 61. After the end cover 61 and the cylinder 62 are sealed, the inlet-outlet 68 is in communication with the negative pressure interface 69 through the filter cartridge 63. The end cover is reliably fixed on the cylinder through structures such as the gasket and the self-locking buckle, to ensure internal sealing and normal operation of the negative pressure system. Quick connectors 93 are disposed on the negative pressure interface 69 of the fat collection tank 6 and the inlet-outlet 68 on the end cover 61.

In this embodiment, in use, in a process in which, the negative pressure generator 94 is started, and under the traction of negative pressure, fat enters the fat inlet channel 12 through the large-diameter liposuction tube, then enters the cutting slot 15 from the outlet of the fat inlet channel 12, and is about to fall into the inlet of the fat outlet channel 22, the fat is cut into smaller particles by using high-speed rotating blades of the cutting device 3 of fat particles, the small-particle fat is suctioned out from the fat outlet of this device under the traction of negative pressure and enters the filter cartridge 63 through the inlet-outlet of the fat collection tank, and filtered liquids, such as blood, are suctioned into the negative pressure tank under the traction of negative pressure. After the liposuction is completed, the filter cartridge 63 and the end cover 61 are taken out together from the cylinder 62, a cotton pad or gauze is used to absorb water through the strainer of the filter cartridge, and then the end cover 61 and the filter cartridge 63 are fixed on the cylinder 62. After being locked by the self-locking buckle, the filter cartridge 63 is turned over, to suction fat into a syringe through the inlet-outlet to inject the fat into a body.

What is claimed is:

1. A fat cutter, comprising a fat inlet channel, a fat outlet channel, at least one set of blades disposed between an outlet of the fat inlet channel and an inlet of the fat outlet channel, and a housing that seals a space, wherein the outlet of the fat inlet channel, the inlet of the fat outlet channel, and the at least one set of blades are located in the space, wherein a fat inlet of the fat inlet channel is connected to a large-diameter liposuction tube, and a fat outlet of the fat outlet channel is connected to a high-negative pressure device; and the outlet of the fat inlet channel and the inlet of the fat outlet channel are oppositely provided, and a first gap is provided between the outlet of the fat inlet channel and the inlet of the fat outlet channel to form an annular cutting slot matching a thickness of the at least one set of blades, the outlet of the fat inlet channel is provided above the inlet of the fat outlet channel, and in a working state, cutting edges of the at least one set of blades pass through a line connecting the outlet of the fat inlet channel and the inlet of the fat outlet channel to cut fat particles.

2. The fat cutter according to claim 1, wherein the housing comprises a cutting table and an upper end cover mounted above the cutting table, a fat particle cutting device that drives the at least one set of blades is mounted in the cutting table, the fat inlet channel is provided on the upper end cover, the fat outlet channel is provided at a position of the cutting table corresponding to the fat inlet channel, the upper end cover is sealed and mounted on the cutting table by using a seal to form an assembled state, and in the assembled state, the first gap is provided in a region between the upper end cover and the cutting table to form the annular cutting slot, wherein the outlet of the fat inlet channel and the inlet of the fat outlet channel are located in the region, and the at least one set of blades of the fat particle cutting device is disposed in the annular cutting slot.

3. The fat cutter according to claim 2, wherein the outlet of the fat inlet channel is coaxially provided above the inlet of the fat outlet channel, a first projection of the outlet of the fat inlet channel on a horizontal plane falls within a range of a second projection of the inlet of the fat outlet channel on the horizontal plane, and an axis of the fat inlet channel and the fat outlet channel is parallel to a rotation axis of the at least one set of blades.

4. The fat cutter according to claim 3, wherein the cutting edges and blade faces of the at least one set of blades are perpendicular to the axis of the fat inlet channel and the fat outlet channel.

5. The fat cutter according to claim 2, wherein a height of the annular cutting slot is 2-4 mm.

6. The fat cutter according to claim 2, wherein the fat particle cutting device comprises the at least one set of blades, a blade carrier, a shaft, and a speed-regulating motor, the at least one set of blades are mounted on the blade carrier, the at least one set of blades and the blade carrier are fixed on the shaft by a self-locking nut, the shaft is mounted on the cutting table through a bearing, the bearing and the cutting table, and the shaft and the cutting table are respectively sealed by a sealing ring, and the shaft is connected to the speed-regulating motor by a buffer coupling.

7. The fat cutter according to claim 6, wherein the speed-regulating motor is electrically connected to a controller, and the controller comprises a rotational speed display screen for displaying a rotational speed of the speed-regulating motor, a speed-regulating switch for regulating the rotational speed of the speed-regulating motor a work indicator for displaying a state of the speed-regulating motor, and a power switch for controlling on and off of the speed-regulating motor.

8. The fat cutter according to claim 1, wherein a rotational speed of the at least one set of blades is 2500-3000 rpm.

9. The fat cutter according to claim 1, wherein the liposuction tube comprises a handle and a liposuction cannula, a liposuction channel and an air bleed channel are provided in the handle is further provided on the housing, the air guide channel is in communication with the annular cutting slot, an outlet of the liposuction channel is connected to the fat inlet of the fat inlet channel of the housing by a liposuction pipeline, a connection channel is further provided in the handle, an air bleed hole is provided on an outer side of the handle, a front end of the air bleed channel is in communication with the connection channel, one end of the connection channel is in communication with the air bleed hole provided on the handle, an other end of the connection channel is in communication with the liposuction channel, an angle is formed between the connection channel and the liposuction channel to prevent suctioned fat from entering the connection channel from the liposuction channel, and an outlet end of the air bleed channel is connected to an air inlet of the air guide channel of the housing by an air bleed tub.

10. The fat cutter according to claim 9, wherein the angle between the connection channel and the liposuction channel facing a connector of the liposuction cannula is an acute angle.

11. The fat cutter according to claim 9, wherein a groove that helps to press and seal the air bleed hole with pulp of a thumb is provided in a region of the handle, and the air bleed hole is located in the region.

12. The fat cutter according to claim 1, wherein an inner wall of the annular cutting slot and an inner wall of the inlet of the fat outlet channel are both covered with a soft material layer.

13. The fat cutter according to claim 1, wherein the inlet of the fat outlet channel is smaller than an outlet of the annular cutting slot to form a step, and an inner wall of the step, a first joint between the step and the outlet of the annular cutting slot, and a second joint between the step and the inlet the fat outlet channel are all curved surfaces.

14. An integrated machine fora preparation of in vitro fine-particle fat, comprising the fat cutter according to claim 1, and further comprising a fat collection tank, a negative pressure, and a negative pressure tank set, wherein the fat collection tank comprises a cylinder and a filter cartridge, a top portion of the cylinder is provided with an opening, a bottom portion of the cylinder is provided with a negative pressure interface in communication with an inner cavity of the cylinder, the filter cartridge is formed by a strainer, and diameters of filter holes of the strainer are less than diameters of to-be-filtered fat particles, after the filter cartridge is mounted in the cylinder, there is a second gap between a periphery of the filter cartridge and an inner wall of the cylinder and there is a third gap between a bottom portion of the filter cartridge and the inner wall of the cylinder, a top portion of the filter cartridge is provided with an opening, an end cover is sealed and mounted on the opening of the filter cartridge, the end cover is connected to the cylinder in a sealed manner after the filter cartridge is mounted in the cylinder, an inlet-outlet is provided on the end cover, the fat outlet of the fat outlet channel on the fat cutter is connected to the inlet-outlet of the fat collection tank by a connection pipeline, the negative pressure generator is connected to the negative pressure tank set by a first pipeline, and the negative pressure tank set is connected to the negative pressure interface of the fat collection tank by a second pipeline.

15. The integrated machine for the preparation of the in vitro fine-particle fat according to claim 14, wherein the fat cutter, the negative pressure generator, and the negative pressure tank set are mounted on a support, the fat cutter is mounted on the support through a fixed frame, and a plurality of casters for support are mounted at a bottom portion of the support.

16. The integrated machine for the preparation of the in vitro fine-particle fat according to claim 14, wherein a self-locking buckle is disposed on an outer wall of the cylinder, a gasket is disposed on the end cover, and after the filter cartridge is mounted in the cylinder, the end cover is connected to an opening edge of the cylinder by the gasket, and the end cover is tightly pressed on the opening edge of the cylinder through the self-locking buckle on the cylinder, so that the end cover and the cylinder are sealed.

17. The integrated machine for the preparation of the in vitro fine-particle fat according to claim 14, wherein the filter cartridge comprises a lower strainer and an upper closed cone, and a height of the lower strainer is ⅓-¾ of a height of the filter cartridge.

18. The integrated machine for the preparation of the in vitro fine-particle fat according to claim 14, wherein the housing comprises a cutting table and an upper end cover mounted above the cutting table, a fat particle cutting device that drives the at least one set of blades is mounted in the cutting table, the fat inlet channel is provided on the upper end cover, the fat outlet channel is provided at a position of the cutting table corresponding to the fat inlet channel, the upper end cover is sealed and mounted on the cutting table by using a seal to form an assembled state, and in the assembled state, the first gap is provided in a region between the upper end cover and the cutting table to form the annular cutting slot, wherein the outlet of the fat inlet channel and the inlet of the fat outlet channel are located in the region, and the at least one set of blades of the fat particle cutting device is disposed in the annular cutting slot.

19. The integrated machine for the preparation of the in vitro fine-particle fat according to claim 18, wherein the outlet of the fat inlet channel is coaxially provided above the inlet of the fat outlet channel, a first projection of the outlet of the fat inlet channel on a horizontal plane falls within a range of a second projection of the inlet of the fat outlet channel on the horizontal plane, and an axis of the fat inlet channel and the fat outlet channel is parallel to a rotation axis of the at least one set of blades.

20. The integrated machine for the preparation of the in vitro fine-particle fat according to claim 19, wherein the cutting edges and blade faces of the at least one set of blades are perpendicular to the axis of the fat inlet channel and the fat outlet channel.

* * * * *